United States Patent
Boettner

(10) Patent No.: US 6,667,393 B2
(45) Date of Patent: Dec. 23, 2003

(54) AZALIDE ANTIBIOTIC COMPOSITIONS

(75) Inventor: Wayne A. Boettner, Noank, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/194,718

(22) Filed: Jul. 11, 2002

(65) Prior Publication Data

US 2003/0073825 A1 Apr. 17, 2003

Related U.S. Application Data

(63) Continuation of application No. 09/768,708, filed on Jan. 24, 2001, now Pat. No. 6,514,945.
(60) Provisional application No. 60/178,481, filed on Jan. 27, 2000.

(51) Int. Cl.[7] .................................................. C07H 17/08
(52) U.S. Cl. ........................................................ 536/7.4
(58) Field of Search ........................................... 536/7.4

(56) References Cited

PUBLICATIONS

Djorkic S. et al., "Journal of the Chemical Society", Perkin Transactions 1, Chemical Society, Letchworth, GB, No. 11, 1986, pp. 1881–1890, XP002077691 ISSN: 1472–7781 p. 1887.*

* cited by examiner

Primary Examiner—Elli Peselev
(74) Attorney, Agent, or Firm—Peter C. Richardson; Gregg C. Benson; Christine S. Lee

(57) ABSTRACT

Antibiotic compositions comprising an equilibrium mixture of azalide isomers, water, and one or more acids, and methods for preparing such compositions, are disclosed. The antibiotic compositions can be advantageously stabilized by adding one or more water-miscible co-solvents. In a preferred embodiment, the one or more co-solvents is propylene glycol.

1 Claim, No Drawings

AZALIDE ANTIBIOTIC COMPOSITIONS

CROSS REFERENCE TO RELATED APPLICATIONS

This application is a continuation of U.S. Ser. No. 09/768,708, filed Jan. 24, 2001, which claims priority to U.S. Ser. No. 60/178,481, filed Jan. 27, 2000 now U.S. Pat. No. 6,514,945 B1 both of which are incorporated herein by reference.

BACKGROUND OF THE INVENTION

This invention relates to pharmaceutical compositions comprising an equilibrium mixture of isomers of an azalide antibiotic compound and to methods for preparing them. This invention further relates to stabilized forms of the aforementioned compositions and to methods of stabilizing them. This invention further relates to methods for treating a mammal comprising administering to a mammal in need of such treatment a pharmaceutical composition of the invention.

Macrolide antibiotic agents active against a wide variety of bacterial and protozoa infections in mammals, fish and birds have been previously reported (see, e.g., International Patent Publications WO 98/56802 and WO 99/12552). These compounds generally have a macrocyclic lactone ring of 12 to 22 carbon atoms to which one or more sugar moieties are attached. Macrolide antibiotics act on the 50S ribosomal subunit to inhibit protein synthesis in microorganisms. Examples of macrolide antibiotics include lincomycin, azithromycin, which is a derivative of erythromycin A, and other azalide compounds.

Development of pharmaceutical compositions containing azalide compounds as the active ingredient has presented significant challenges. Some azalides are capable of isomerizing in solution. Consequently, the production of a reproducible antibiotic composition comprising a single isomer or a fixed ratio of isomers has been difficult. Second, a composition containing a fixed amount of a particular azalide isomer may change over time. Third, the lactone ring and sugars of azalides are easily hydrolyzed in even mildly acidic or basic pH environments, decreasing the potency and shelf-life of an antibiotic composition.

Accordingly, it is an object of the present invention to provide antibiotic compositions, and methods for preparing them, that overcome the above-mentioned disadvantages.

Citation of any reference herein shall not be construed as indicating that such reference is prior art to the present invention.

SUMMARY OF THE INVENTION

In a first embodiment, the present invention relates to a composition comprising: (a) the compound of formula I

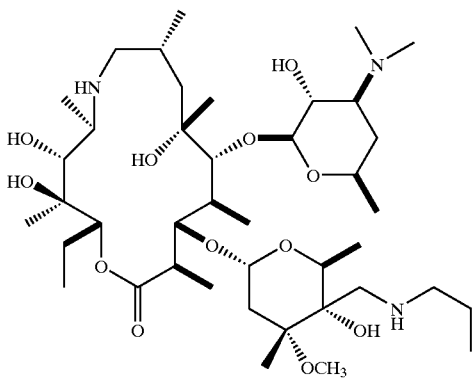

(I)

and the compound of formula II:

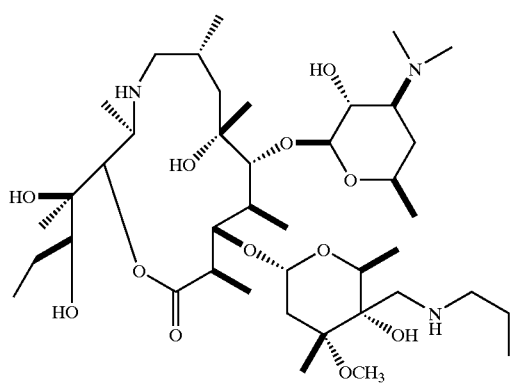

(II)

in a ratio of about 90% ±4% to about 10%±4%, respectively; (b) water; and (c) one or more acids present at a total concentration of from about 0.2 mmol to about 1.0 mmol per mL of the composition.

The present invention relates to a method for obtaining a composition comprising: (a) the compound of formula I and the compound of formula II in a ratio of about 90%±4% to about 10%±4%, respectively; (b) water; and (c) one or more acids present at a total concentration of from about 0.2 mmol to about 1.0 mmol per mL of the composition, comprising the step of heating to a temperature of about 50° C. to about 90° C. a mixture comprising: (i) the compound of formula (I), (ii) water, and (iii) one or more acids in a total amount ranging from about 0.2 mmol to about 1.0 mmol per mL of the mixture.

The present invention relates to a composition comprising: (a) a mixture comprising: (i) the compound of formula (I) and the compound of formula (II) in a ratio of about 90%±4% to about 10%±4%, respectively; (ii) water; and (iii) one or more acids present at a total concentration of from about 0.2 mmol to about 1.0 mmol per mL of the mixture; and (b) one or more water-miscible co-solvents present in a total amount of from about 250 to about 750 mg per mL of the composition.

The present invention relates to a method for obtaining a composition comprising: (a) a mixture comprising: (i) the compound of formula (I) and the compound of formula (II) in a ratio of about 90%±4% to about 10%±4%, respectively; (ii) water; and (iii) one or more acids present at a total concentration of from about 0.2 mmol to about 1.0 mmol per mL of the mixture; and (b) one or more water-miscible co-solvents present in a total amount of from about 250 to about 750 mg per mL of the composition, comprising heating to a temperature of about 50° C. to 90° C. a mixture comprising the compound of formula (I), water and one or more acids in an amount ranging from about 0.2 mmol to about 1.0 mmol per mL of the mixture, wherein one or more water-miscible co-solvents is added before, during or after the heating step, in an amount of from about 250 to about 750 mg per mL of the composition. In a preferred embodiment, the water-miscible co-solvent is added after the heating step.

The present invention relates to a method for preserving the structural integrity of the compound of formula I or the compound of formula II comprising the step of forming a composition by adding one or more water-miscible co-solvents to a mixture comprising: (a) the compound of formula (I) and the compound of formula (II); (b) water; and (c) one or more acids present in a total amount of from about 0.2 mmol to about 1.0 mmol per mL of the mixture, the amount of added water-miscible co-solvent being about 250 to about 750 mg per mL of the composition.

In an embodiment of any of the above methods, the pH of the mixture ranges from about 5.0 to about 8.0, and more preferably, from about 5.0 to about 6.0.

In an embodiment of any of the above methods, the heating takes place for about 0.5 to about 24 hours, and more preferably, from about 1 to about 8 hours.

In an embodiment of any of the compositions or methods of the invention, the concentration of the compound of formula (I) in the mixture, i.e., before the heating step, ranges from about 50 mg to about 500 mg per mL of the mixture. In a preferred embodiment thereof, the concentration ranges from about 50 mg/mL to about 200 mg/mL.

In an embodiment of any of the compositions or methods of the invention the concentration of the first mixture (of compound I and compound II) in the composition ranges from about 50 mg/mL to about 200 mg/mL of the composition. In a preferred embodiment thereof, the concentration of the first mixture in the composition ranges from about 75 to about 150 mg/mL, and more preferably from about 90 mg/mL to about 110 mg/mL of the composition.

In an embodiment of any of the compositions or methods of the invention, the one or more acids are selected from the group consisting of acetic acid, benzenesulfonic acid, citric acid, hydrobromic acid, hydrochloric acid, D- and L-lactic acid, methanesulfonic acid, phosphoric acid, succinic acid, sulfuric acid, D- and L-tartaric acid, p-toluenesulfonic acid, adipic acid, aspartic acid, camphorsulfonic acid, 1,2-ethanedisulfonic acid, laurylsulfuric acid, glucoheptonic acid, gluconic acid, 3-hydroxy-2-naphthoic acid, 1-hydroxy-2-naphthoic acid, 2-hydroxyethanesulfonic acid, malic acid, mucic acid, nitric acid, naphthalenesulfonic acid, palmitic acid, D-glucaric acid, stearic acid, maleic acid, malonic acid, fumaric acid, benzoic acid, cholic acid, ethanesulfonic acid, glucuronic acid, glutamic acid, hippuric acid, lactobionic acid, lysinic acid, mandelic acid, napadisylic acid, nicotinic acid, polygalacturonic acid, salicylic acid, sulfosalicylic acid, tryptophanic acid, and mixtures thereof. In a preferred embodiment thereof, the one or more acids is citric acid. In a more preferred embodiment thereof, the citric acid is present in an amount of from about 0.02 mmol to about 0.3 mmol per mL of composition. In another preferred embodiment thereof, the one or more acids are citric acid and hydrochloric acid. In a more preferred embodiment thereof, citric acid is present in an amount of from about 0.02 mmol to about 0.3 mmol per mL of composition and the hydrochloric acid is present in an amount sufficient to achieve a composition pH of about 5 to about 6.

In an embodiment of any of the compositions or methods of the invention, the one or more water-miscible co-solvents are selected from the group consisting of ethanol, isopropanol, diethylene glycol monomethyl ether, diethylene glycol butyl ether, diethylene glycol monoethyl ether, diethylene glycol dibutyl ether, polyethylene glycol-300, polyethylene glycol-400, propylene glycol, glycerine, 2-pyrrolidone, N-methyl 2-pyrrolidone, glycerol formal, dimethyl sulfoxide, dibutyl sebecate, polysorbate 80, and mixtures thereof. In a preferred embodiment thereof, the one or more water-miscible co-solvents is propylene glycol. In a more preferred embodiment thereof, the propylene glycol is present in an amount of from about 450 to about 550 mg per mL of the composition.

In an embodiment of any of the compositions or methods of the invention, the composition further comprises one or more antioxidants present in an amount of from about 0.01 mg to about 10 mg per mL of the composition. In a preferred embodiment thereof, the one or more antioxidants is selected from the group consisting of sodium bisulfite, sodium sulfite, sodium metabisulfite, sodium thiosulfate, sodium formaldehyde sulfoxylate, L-ascorbic acid, erythorbic acid, acetylcysteine, cysteine, monothioglycerol, thioglycollic acid, thiolactic acid, thiourea, dithiothreitol, dithioerythreitol, glutathione, ascorbyl palmitate, butylated hydroxyanisole, butylated hydroxytoluene, nordihydroguaiaretic acid, propyl gallate, α-tocopherol, and mixtures thereof. In a more preferred embodiment thereof, the one or more antioxidants is monothioglycerol. In an especially preferred embodiment thereof, monothioglycerol is present in an amount of from about 4 mg/mL to about 6 mg/mL of the composition.

In an embodiment of any of the compositions or methods of the invention, the composition further comprises one or more preservatives. In a preferred embodiment thereof, the one or more preservatives are present in an amount of from about 0.01 to about 10 mg per mL of the pharmaceutical compositions. Preferably, the one or more preservatives is phenol and present in an amount of from about 2.0 to about 5.0 mg per mL, more preferably, from about 2.0 to about 3.0 mg per mL, of the pharmaceutical compositions. In another preferred embodiment thereof, the one or more preservatives are selected from benzalkonium chloride, benzethonium chloride, benzoic acid, benzyl alcohol, methylparaben, ethylparaben, propylparaben, butylparaben, sodium benzoate, phenol, and mixtures thereof. In a more preferred embodiment thereof, the one or more preservatives are selected from the group consisting of benzyl alcohol, methylparaben, propylparaben, a methylparaben/propylparaben combination, and phenol. In a particularly preferred embodiment thereof, the preservative is phenol. In a still further embodiment thereof, the preservative is phenol present in an amount of from about 2.0 to about 3.0 mg per mL of the pharmaceutical composition.

In an especially preferred embodiment of the composition of this invention, the one or more acids are citric acid present in an amount of from about 0.02 mmol to about 0.3 mmol per mL of composition and hydrochloric acid is present in an amount sufficient to achieve a composition pH of about 5 to about 6; the one or more water-miscible co-solvents is propylene glycol present in an amount of from about 450 to about 550 mg per mL of the composition, and the composition further comprises the antioxidant monothioglycerol present in an amount of from about 4 mg/mL to about 6 mg/mL of the composition.

The present invention relates to a method for treating a bacterial or protozoal infection in a mammal, comprising administering to a mammal in need of such treatment a therapeutically effective amount of a composition comprising: (a) the compound of formula I and the compound of formula II in a ratio of about 90%±4% to about 10%±4%, respectively, (b) water; and (c) one or more acids present at a total concentration of from about 0.2 mmol to about 1.0 mmol per mL of the composition.

The present invention also relates to a method for treating a bacterial or protozoal infection in a mammal, comprising administering to a mammal in need of such treatment an effective amount of a composition comprising: (a) a mixture comprising: (i) the compound of formula (I) and the compound of formula (II) in a ratio of about 90%±4% to about 10%±4%, respectively; (ii) water; and (iii) one or more acids present at a total concentration of from about 0.2 mmol to about 1.0 mmol per mL of the mixture; and (b) one or more water-miscible co-solvents present in a total amount of from about 250 to about 750 mg per mL of the composition.

In another preferred embodiment, the bacterial or protozoal infection is selected from the group consisting of bovine respiratory disease, swine respiratory disease, pneumonia, coccidiosis, anaplasmosis, and infectious keratinitis. In other preferred embodiments, the method comprises administering to a mammal in need of such treatment a therapeutically effective amount of any of the compositions or embodiments thereof described herein.

wherein $R^1$ is OH or

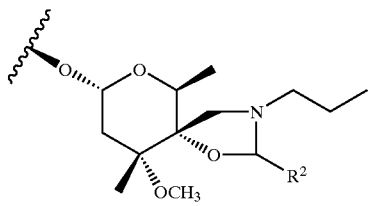

and wherein $R^2$ is H or $CH_3$. In a preferred embodiment thereof, $R^1$ is OH. In another preferred embodiment thereof, $R^2$ is H. In another preferred embodiment thereof, $R^2$ is $CH_3$.

The present invention may be understood more fully by reference to the detailed description and illustrative examples which are intended to exemplify non-limiting embodiments of the invention.

DETAILED DESCRIPTION OF THE INVENTION

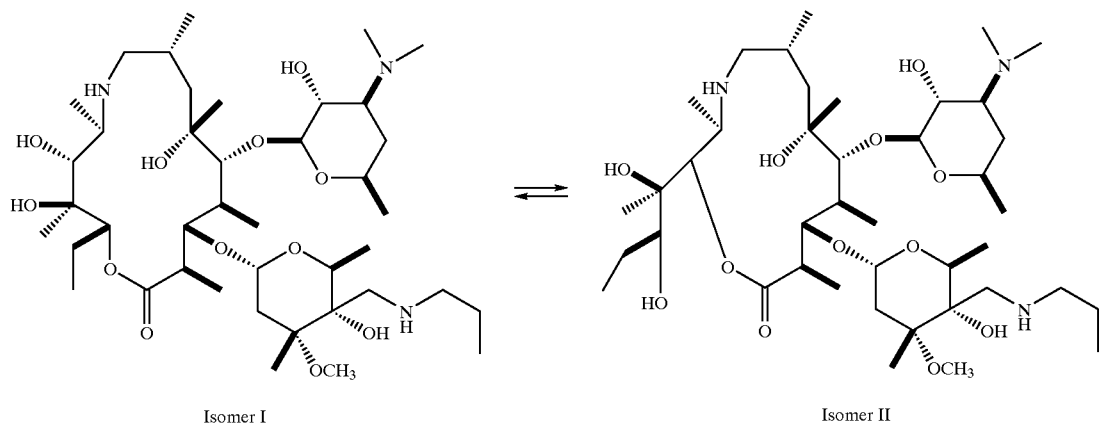

Isomer I ⇌ Isomer II

This invention also relates to a compound of the formula:

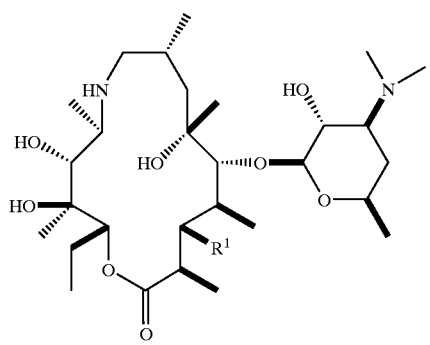

or a pharmaceutically acceptable salt thereof;

The present invention relates to pharmaceutical compositions comprising isomer I and isomer II (collectively the "azalide isomers") in a ratio of about 90%±4% to about 10%±4%. The chemical name of isomer I is (2R,3S,4R,5R, 8R,10R,11R,12S,13S,14R)-13-((2,6-dideoxy-3-C-methyl-3-O-methyl-4-C-((propylamino)-methyl)-α-L-ribo-hexopyranosyl)oxy-2-ethyl-3,4,10-trihydroxy-3,5,8,10,12,14-hexamethyl-11-((3,4,6-trideoxy-3-(dimethylamino)-β-D-xylo-hexopyranosyl)oxy)-1-oxa-6-azacyclopentadecan-15-one. The chemical name of isomer II is (3R,6R,8R,9R,10S,11S,12R)-11-((2,6-dideoxy-3-C-methyl-3-O-methyl-4-C-((propylamino)methyl-α-L-ribo-hexopyranosyl)oxy)-2-((1R,2R)-1,2-dihydroxy-1-methylbutyl)-8-hydroxy-3,6,8,10,12-pentamethyl-9-((3,4,6-trideoxy-3-(dimethylamino)-β-D-xylohexopyranosyl)oxy)-1-oxa-4-azacyclotridecan-13-one. Isomer I can be formed from a translactonization reaction of isomer II. Likewise, isomer II can be formed from a translactonization reaction of isomer I. Methods for obtaining isomer I are disclosed in International publication no. WO 98/56802, incorporated herein by reference. Methods for obtaining isomer II are in disclosed Example 1, below. The azalide isomers are active antibiotic agents.

Without being bound by any theory, the invention is based in part on Applicant's surprising discovery that a composition comprising isomer I and isomer II in a ratio of about 90%±4% to about 10%±4% can be obtained rapidly using the methods disclosed herein independent of the starting ratio of the azalide isomers. While not absolutely certain, applicant believes that the about 90%±4% to about 10%±4% ratio of isomer I and isomer II constitutes an equilibrium mixture of the azalide isomers. Accordingly, the term "equilibrium mixture of isomers" as used herein refers to a mixture of isomer I and isomer II in a ratio of about 90%±4% to about 10%±4%, respectively. An antibiotic composition comprising the equilibrium mixture of isomers can be consistently produced and provides a standard for testing or consumer use. Thus, a composition comprising the equilibrium mixture of isomers is highly desirable.

The present invention further relates to a method for preparing a composition comprising an equilibrium mixture of isomers. In one embodiment, the equilibrium mixture of isomers is obtained from a solution of substantially pure isomer I. By "substantially pure", as used herein, unless otherwise indicated, is meant having a purity of at least 97%. In another embodiment, the equilibrium mixture of isomers is obtained from a solution comprising a mixture of isomer I and isomer II. In general, an equilibrium mixture of isomers is generated by heating a water solution of isomer I, preferably substantially pure isomer I, or a mixture of isomer I and isomer II, in the presence of one or more acids. In a preferred embodiment, a water solution of isomer I and one or more acids is heated to a temperature of between about 50° C. to about 90° C., preferably about 60° C. to about 80° C., for about 0.5 to about 24 hours, preferably about 1 to about 10 hours, at a pH of about 5.0 to about 8.0, preferably from about 6.0 to about 8.0. Most preferably, a solution of isomer I and isomer II is heated to a temperature of between about 65° C. to about 75° C. for about 1 to about 8 hours at a pH of about 6.5 to 7.5 in the presence of one or more acids. The concentration of isomer I or the mixture of isomer I and isomer II to be equilibrated can vary from about 50 mg/mL to about 500 mg/mL, preferably from about 100 mg/mL to about 300 mg/mL, and most preferably from about 225 mg/mL to about 275 mg/mL of solution.

Suitable acids useful for obtaining the equilibrium mixture of isomers include, but are not limited to, acetic acid, benzenesulfonic acid, citric acid, hydrobromic acid, hydrochloric acid, D- and L-lactic acid, methanesulfonic acid, phosphoric acid, succinic acid, sulfuric acid, D- and L-tartaric acid, p-toluenesulfonic acid, adipic acid, aspartic acid, camphorsulfonic acid, 1,2-ethanedisulfonic acid, laurylsulfuric acid, glucoheptonic acid, gluconic acid, 3-hydroxy-2-naphthoic acid, 1-hydroxy-2-naphthoic acid, 2-hydroxyethanesulfonic acid, malic acid, mucic acid, nitric acid, naphthalenesulfonic acid, palmitic acid, D-glucaric acid, stearic acid, maleic acid, malonic acid, fumaric acid, benzoic acid, cholic acid, ethanesulfonic acid, glucuronic acid, glutamic acid, hippuric acid, lactobionic acid, lysinic acid, mandelic acid, napadisylic acid, nicotinic acid, polygalacturonic acid, salicylic acid, sulfosalicylic acid, tryptophanic acid, and mixtures thereof. Preferably, the one or more acids are citric and hydrochloric acid. When present, citric acid is present at a concentration of from about 0.02 mmol to about 0.3 mmol per mL of solution. In one embodiment, an acid concentration of from about 0.2 mmol to about 1.0 mmol per mL of solution is used. Without being bound by any theory, applicant believes the salt formed from the addition of an acid to a solution of isomer I exerts a buffering effect, because the azalide isomers themselves act as a base. Those of skill in the art will recognize that the amount of acid required for a desired pH will vary according to which acid is used, and that, in order to maintain a pH within the desired range, additional acid and/or a base may be added to the solution of acid and isomer I, or mixture of isomer I and isomer II. Suitable bases include, but are not limited to, alkali metal hydroxides and carbonates, alkali metal bicarbonates, and alkaline earth hydroxides and carbonates. Sodium hydroxide and potassium hydroxide are preferred. The acids and bases described above are conveniently used in the form of their aqueous solutions.

Compositions comprising the equilibrium mixture of isomers (the "equilibrated compositions") are useful for treating a bacterial or protozoal infection in a mammal. The equilibrated compositions are also useful as intermediates for the formation of stabilized, equilibrated compositions.

The present invention further relates to stabilized, equilibrated compositions and to methods of stabilizing them comprising diluting the equilibrated compositions with one or more water-miscible organic solvents ("co-solvent"). The co-solvent does not significantly affect the ratio of isomer I and isomer II in the equilibrated compositions, and in fact preserves their structural integrity. "Preserving the structural integrity" of isomer I or isomer II as used herein, includes, but is not limited to, retarding their rate of hydrolysis to, for example, descladinose azalide, and retarding their rate of byproduct formation of, for example, a formaldehyde and an acetaldehyde insertion product, defined below. Without being bound by any theory, Applicant believes that dilution with co-solvent improves the stability of the azalide isomers. Moreover, by virtue of the presence of co-solvent, any pain experienced upon injection of the stabilized, equilibrated compositions may be less than that experienced from injection of an equilibrated composition not so stabilized. Co-solvents useful for stabilizing the equilibrated compositions include, but are not limited to, alcohols such as ethanol and isopropanol; glycol ethers such as diethylene glycol monomethyl ether, diethylene glycol butyl ether, diethylene glycol monoethyl ether and diethylene glycol dibutyl ether; polyethylene glycols such as polyethylene glycol-300 and polyethylene glycol-400; glycols such as propylene glycol ("PG") and glycerine; pyrrolidones such as 2-pyrrolidone and N-methyl 2-pyrrolidone; glycerol formal; dimethyl sulfoxide; dibutyl sebecate; polyoxyethylene sorbitan esters such as polysorbate 80; and mixtures thereof. Preferably, co-solvents useful for stabilizing the equilibrated compositions in injectable solutions include, but are not limited to, ethanol, polyethylene glycols such as polyethylene glycol-300 and polyethylene glycol-400, glycols such as propylene glycol and glycerine, pyrrolidones such as 2-pyrrolidone and N-methyl 2-pyrrolidone, glycerol formal, dimethyl sulfoxide, polyoxyethylene sorbitan esters such as polysorbate 80, and mixtures thereof, more preferably, glycerol formal, N-methyl 2-pyrrolidone and propylene glycol, and most preferably, propylene glycol. In one embodiment, co-solvent in an amount of about 250 to about 750 mg per mL of the pharmaceutical compositions is used to stabilize them. In a preferred embodiment, about 400 to about 600 mg of co-solvent per mL of the pharmaceutical compositions is used. In a most preferred embodiment, about 450 to about 550 mg of co-solvent per mL of the pharmaceutical compositions is used.

In one embodiment, one or more co-solvents are added to isomer I or to a mixture of isomer I and isomer II prior to equilibration. In this case, the resulting mixture is heated to a temperature of between about 50° C. to about 90° C., preferably about 60° C. to about 80° C., for about 0.5 to about 24 hours, preferably for about 1 to about 10 hours, at a pH of about 5.0 to about 8.0, preferably at a pH of about 6.0 to about 8.0. In a preferred embodiment, equilibration of the azalide isomers is carried out in the absence of co-solvent, which is added to the equilibrated compositions after they have cooled to about room temperature.

After addition of the co-solvent, the pH of the resulting solution can be re-adjusted to further improve stability of the composition. The pH is adjusted by methods known to those skilled in the art, such as for example by adding an amount of acid or base described above, e.g., as a 10% (w/w) stock solution, and measuring the pH of the resulting solution using, e.g., a pH meter. In one embodiment, the pH of the resulting solution, if necessary, is adjusted to about 4.5 to about 7.5, preferably about 5.0 to about 6.0, most preferably, about 5.2 to about 5.6.

The present invention further relates to pharmaceutical compositions comprising an equilibrium mixture of isomers, water, one or more acids, and one or more water-miscible co-solvents. The amount of azalide isomers in the pharmaceutical compositions ranges from about 50 mg of azalide isomers per mL of pharmaceutical composition to about 200 mg of azalide isomers per mL of pharmaceutical composition. Preferably, the pharmaceutical compositions comprise from about 75 mg to about 150 mg, more preferably, from about 90 to about 110 mg, of azalide isomers per mL of pharmaceutical composition.

The pharmaceutical compositions can still further comprise one or more antioxidants. Antioxidants retard the rate of or prevent oxidative breakdown of the pharmaceutical compositions. Suitable antioxidants include, but are not limited to, sodium bisulfite, sodium sulfite, sodium metabisulfite, sodium thiosulfate, sodium formaldehyde sulfoxylate, L-ascorbic acid, erythorbic acid, acetylcysteine, cysteine, monothioglycerol ("MTG"), thioglycollic acid, thiolactic acid, thiourea, dithiothreitol, dithioerythreitol, glutathione, ascorbyl palmitate, butylated hydroxyanisole, butylated hydroxytoluene, nordihydroguaiaretic acid, propyl gallate, α-tocopherol, and mixtures thereof. Those of skill in the art will recognize that the amount of antioxidant will vary according to which antioxidant is used. In a preferred embodiment, the antioxidant, when present, is present in an amount of from about 0.01 mg to about 10 mg per mL of pharmaceutical composition. In a more preferred embodiment, the antioxidant is monothioglycerol and present in an amount of from about 1 mg to about 8 mg per mL of pharmaceutical composition. In a most preferred embodiment, the antioxidant is monothioglycerol and present in an amount of from about 4 mg to about 6 mg per mL of pharmaceutical composition.

The pharmaceutical compositions optionally comprise one or more preservatives. Preservatives are useful for retarding the rate of or preventing proliferation of microorganisms, particularly when the pharmaceutical compositions are exposed to air. Useful preservatives are: effective against a broad spectrum of microorganisms; physically, chemically and microbiologically stable over the lifetime of the pharmaceutical compositions; non-toxic; adequately soluble; compatible with other components of the composition; and acceptable with respect to taste and odor. Suitable preservatives include, but are not limited to, benzalkonium chloride, benzethonium chloride, benzoic acid, benzyl alcohol, methylparaben, ethylparaben, propylparaben, butylparaben, sodium benzoate, phenol, and mixtures thereof. In a preferred embodiment, the one or more preservatives are selected from the group consisting of benzyl alcohol, methylparaben, propylparaben, a methylparaben/ propylparaben combination, and phenol. When present, the one or more preservatives are present in an amount of from about 0.01 to about 10 mg per mL of the pharmaceutical compositions. Preferably, the one or more preservatives is phenol and present in an amount of from about 2.0 to about 5.0 mg per mL, more preferably, from about 2.0 to about 3.0 mg per mL, of the pharmaceutical compositions. One of skill in the art will recognize that the amount of preservative to be used in the present compositions will depend on which preservative is chosen, and that some preservatives may be used at lower concentrations, even lower than about 0.01 mg per mL of the pharmaceutical compositions.

In a preferred embodiment, the pharmaceutical compositions of the invention have a pH of from about 5.0 to about 7.0 and comprise: (1) an equilibrium mixture of isomers present in an amount of from about 50 mg to about 200 mg per mL of the pharmaceutical composition; (2) citric acid present in a concentration of from about 0.02 mmol to about 0.3 mmol per mL of the pharmaceutical composition and, optionally, an amount of hydrochloric acid effective to achieve the pH range; (3) propylene glycol, present in an amount of from about 250 to about 750 mg per mL of the pharmaceutical composition; (4) monothioglycerol, present in an amount of from about 1 mg to about 15 mg per mL of the pharmaceutical composition; and (5) water, present in an amount of from about 100 to about 750 mg per mL of the pharmaceutical composition.

In a more preferred embodiment, the pharmaceutical compositions of the invention have a pH of from about 5.0 to about 6.0 and comprise: (1) an equilibrium mixture of isomers present in an amount of from about 75 mg to about 150 mg per mL of the pharmaceutical composition; (2) citric acid present in an amount of from about 0.05 mmol to about 0.15 mmol per mL of the pharmaceutical composition and, optionally, an amount of hydrochloric acid effective to achieve the pH range; (3) propylene glycol, present in an amount of from about 400 to about 600 mg per mL of the pharmaceutical composition; (4) monothioglycerol, present in an amount of from about 1 mg to about 8 mg per mL of the pharmaceutical composition; and (5) water, present in an amount of from about 250 to about 550 mg per mL of the pharmaceutical composition.

In a most preferred embodiment, the pharmaceutical compositions of the invention have a pH of from about 5.2 to about 5.6 and comprise: (1) an equilibrium mixture of isomers present in an amount of from about 90 mg to about 110 mg per mL of the pharmaceutical composition; (2) citric acid present in an amount of from about 0.075 mmol to about 0.125 mmol per mL of the pharmaceutical composition, and an amount of hydrochloric acid effective to achieve the pH range; (3) propylene glycol, present in an amount of from about 450 to about 550 mg per mL of the pharmaceutical composition; (4) monothioglycerol, present in an amount of from about 4 mg to about 6 mg per mL of the pharmaceutical composition; and (5) water, present in an amount of from about 300 to about 500 mg per mL of the pharmaceutical composition.

The pharmaceutical compositions can be prepared as follows. Reagents are added in a stainless steel- or glass-lined jacketed vessel with optional nitrogen overlay. Water for Injection is added to the reaction vessel, and agitation is begun. Each additional component is added while the mixture is continuously agitated. Acid in a concentration of about 0.02 mmol to about 0.5 mmol per mL of water is added and allowed to dissolve. An aqueous solution of an acid, e.g., a 10% (w/w) aqueous solution of hydrochloric acid, is optionally added to adjust the pH to a desired range and the solution is mixed. At this point, isomer I, or a mixture of isomer I and isomer II, is added to the water and acid mixture slowly and in small quantities to avoid clumping. Isomer I, or a mixture of isomer I and isomer II, is allowed to dissolve, and the pH of the resulting solution is measured. In one embodiment, the concentration of isomer I or the mixture of isomer I and isomer II is from about 50 mg to about 500 mg per mL, preferably from about 100 to about 300 mg per mL, and most preferably from about 225 to about 275 mg per mL, of the resulting solution. The solution is then heated to a temperature of about 70° C.±10° C. and is maintained at this temperature until an equilibrium mixture of isomers is obtained. Methods for determining that an equilibrium mixture of isomers has been obtained include gel chromatography, thin-layer chromatography, and high-performance liquid chromatography. Generally, using the conditions described herein, an equilibrium mixture of isomers is obtained in about 1 to about 8 hours. Once the equilibrium mixture of isomers is obtained, the resulting solution is cooled to about 25° C.±10° C. This solution can be used as a pharmaceutical composition. Preferably, co-solvent is added in an amount of from about 250 to about 750 mg per mL of the pharmaceutical composition. Anti-oxidant is optionally added in an amount of from about 0.01 mg to about 10 mg per mL of the pharmaceutical composition. If present, preservative is added in an amount of from about 0.01 to about 10 mg per mL of the pharmaceutical composition, and the pH is adjusted to about 5.0 to about 8.0, preferably to about 5.0 to about 6.0, by adding acid and/or base, for example, as a 10% (w/w) aqueous solution or in solid form. The resulting mixture is diluted to a desired volume. In one embodiment, the final concentration of the equilibrium mixture of isomers is about 50 mg to about 200 mg, preferably about 75 mg to about 150 mg, and most preferably about 90 mg to about 110 mg per mL of the resulting pharmaceutical composition.

The resulting compositions are preferably sterilized, for example, by passing the compositions through a pre-filter, e.g., a 5–10 micron filter and then through a 0.2 micron final sterilizing filter that has been previously sterilized. The sterilizing filter is sterilized by moist-heat autoclaving for 60 minutes at 121° C., and is tested for integrity using a pressure-hold method prior to sterilization and after product filtration. The sterile solution is added to suitable containers, e.g., glass vials, that are sterilized and depyrogenated at 250° C. for 240 minutes in a dry-heat tunnel. The container head-space is flushed with an inert gas, e.g., argon or preferably, nitrogen. The containers are capped with stoppers that are depyrogenated by washing and sterilized by moist-heat autoclaving for 60 minutes at 121° C. The containers are then over-sealed. Those skilled in the art will recognize that minor modifications to the above can be used to prepare sterile compositions.

The present invention further relates to methods for treating a mammal, comprising administering to a mammal in need of such treatment a pharmaceutically effective amount of a pharmaceutical composition of the invention. The pharmaceutical compositions of the invention can be used to treat infections by gram-positive bacteria, gram-negative bacteria, protozoa, and mycoplasma, including, but not limited to, *Actinobacillus pleuropneumonia, Pasteurella multocida, Pasteurella haemolytica, H. parasuis, B. bronchiseptica, S. choleraesuis, S. pilo, Moraxella bovis, H. somnus, M. bovis, Eimeria zuernii, Eimeria bovis, A. marginale, M. hyopneumoniae, Lawsonia intracellularis,* and staphylococcus, salmonella, chlamydia, coccidia, cryptosporidia, *E. coli,* haemophilus, neospora, and streptococcus species.

The term "treatment", as used herein, unless otherwise indicated, includes the treatment or prevention of a bacterial infection or protozoal infection as provided in the method of the present invention.

As used herein, unless otherwise indicated, the terms "bacterial infection(s)" and "protozoal infection(s)" include bacterial infections and protozoal infections that occur in mammals, fish and birds as well as disorders related to bacterial infections and protozoal infections that may be treated or prevented by administering antibiotics such as the compounds of the present invention. Such bacterial infections and protozoal infections, and disorders related to such infections, include the following: pneumonia, otitis media, sinusitis, bronchitis, tonsillitis, and mastoiditis related to infection by *Streptococcus pneumoniae, Haemophilus influenzae, Moraxella catarrhalis, Staphylococcus aureus,* or *Peptostreptococcus* spp.; pharynigitis, rheumatic fever, and glomerulonephritis related to infection by *Streptococcus pyogenes,* Groups C and G streptococci, *Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal groups C–F (minute-colony streptococci), viridans streptococci, *Corynebacterium minutissimum,* Clostridium spp., or *Bartonella henselae,* uncomplicated acute urinary tract infections related to infection by *Staphylococcus saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum,* or *Neiserria gonorrheae;* toxin diseases related to infection by *S. aureus* (food poisoning and Toxic shock syndrome), or Groups A, B, and C streptococci, ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *Chlamydia trachomatis, Neisseria gonorrhoeae, S. aureus, S. pneumoniae, S. pyogenes, H. influenzae,* or Listeria spp.; disseminated *Mycobacterium avium* complex (MAC) disease related to infection by *Mycobacterium avium,* or *Mycobacterium intracellulare;* gastroenteritis related to infection by *Campylobacter jejuni;* intestinal protozoa related to infection by Cryptosporidium spp.; odontogenic infection related to infection by viridans streptococci; persistent cough related to infection by *Bordetella pertussis;* gas gangrene related to infection by *Clostridium perfringens* or Bacteroides spp.; and atherosclerosis related to infection by *Helicobacter pylori* or *Chlamydia pneumoniae.* Bacterial infections and protozoal infections and disorders related to such infections that may be treated or prevented in animals include the following: bovine respiratory disease related to infection by *P. haem., P. multocida, Mycoplasma bovis,* or Bordetella spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae,* Klebsiella spp., Corynebacterium, or Enterococcus spp.; swine respiratory disease related to infection by *A. pleuro., P. multocida,* or Mycoplasma spp.; swine enteric disease related to infection by *E. coli, Lawsonia intracellularis,* Salmonella, or *Serpulina hyodyisinteriae;* cow footrot related to infection by Fusobacterium spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *Staph. epidermidis, Staph. intermedius*, coagulase neg. Staph. or *P. multocida*; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoal infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

The antibacterial and antiprotozoal activity of the compounds of the present invention against bacterial and protozoa pathogens is demonstrated by the compounds' ability to inhibit growth of defined strains of human or animal pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compounds' ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2N-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The assay is performed in microtiter trays and interpreted according to Performance Standards for Antimicrobial Disk Susceptibility Tests—Sixth Edition; Approved Standard, published by The National Committee for Clinical Laboratory Standards (NCCLS) guidelines; the minimum inhibitory concentration (MIC) is used to compare strains. The equilibrium mixture of azalide isomers is initially dissolved in dimethylsulfoxide (DMSO) as a 40 mg/ml stock solution.

| Strain Designation | Macrolide Resistance Mechanism(s) |
|---|---|
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | ermB |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Streptococcus pneumoniae* 0085 | susceptible |
| *Haemophilus influenzae* 0131 | susceptible |
| *Moraxella catarrhalis* 0040 | susceptible |
| *Moraxella catarrhalis* 1055 | Erythromycin intermediate resistance |
| *Escherichia coli* 0266 | susceptible |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The equilibrium mixture of azalide isomers is prepared by solubilizing 1 mg of the mixture in 125 $\mu$l of dimethylsulfoxide (DMSO). Dilutions of the equilibrium mixture of azalide isomers are prepared using uninoculated BHI broth. The concentrations of the equilibrium mixture of azalide isomers used range from 200 $\mu$g/mL to 0.098 $\mu$g/mL by two-fold serial dilutions. The *P. multocida* inoculated BHI is diluted with uninoculated BHI broth to make a $10^4$ cell suspension per 200 $\mu$L. The BHI cell suspensions are mixed with respective serial dilutions of the equilibrium mixture of azalide isomers, and incubated at 37° C. for 18 hours. The minimum inhibitory concentration (MIC) is equal to the concentration of the mixture exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 $\mu$L of the fully grown *P. haemolytica* preculture is inoculated into 3 ml of fresh BHI broth and is incubated at 37° C. with shaking (200 rpm). The appropriate amounts of the equilibrium mixture of azalide isomers are dissolved in ethanol and a series of two-fold serial dilutions are prepared. Two mL of the respective serial dilution is mixed with 18 mL of molten BHI agar and solidified. When the inoculated *P. haemolytica* culture reaches 0.5 McFarland standard density, about 5 $\mu$L of the *P. haemolytica* culture is inoculated onto BHI agar plates containing the various concentrations of the equilibrium mixture of azalide isomers using a Steers Replicator and incubated for 18 hours at 37° C. Initial concentrations of the mixture range from 100–200 μg/mL. The MIC is equal to the concentration of the mixture exhibiting 100% inhibition of growth of *P. haemolytica* as determined by comparison with an uninoculated control.

Most preferably, the microdilution assay is performed using cation-adjusted Mueller-Hinton broth according to NCCLS guideline M31-A, Vol. 19, No. 11, "Performance standards for antimicrobial disk and dilution susceptibility tests for bacteria isolated from animals," June 1999 (ISBN 1-56238-377-9), which is herein incorporated by reference. This assay may be used to determine the MIC of a compound against both *P. haemolytica* and *P. multocida*. For example, the equilibrium mixture of isomers was tested according to this standard, against *P. haemolytica* (ATCC 14003), and found to have a MIC of 1 μg/mL. When the equilibrium mixture of isomers was tested according to this standard, against *P. multocida* (ATCC 43137), the MIC was found to be 1 μg/mL.

Assay IV

The in vivo activity of the pharmaceutical compositions of the present invention can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a 3×10$^3$ CFU/ml bacterial suspension (*P. multocida* strain 59A006) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall syringe) is used to administer the challenge. Thirty minutes after challenging has begun, the first pharmaceutical composition treatment is given. It may be necessary for a second person to begin pharmaceutical composition dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compositions are administered 30 minutes, 4 hours, and 24 hours after challenge. A control composition of known efficacy administered by the same route is included in each test. Animals are observed daily, and the number of survivors in each group is recorded. The *P. multocida* model monitoring continues for 96 hours (four days) post challenge.

The PD$_{50}$ is a calculated dose at which the pharmaceutical composition tested protects 50% of a group of mice from mortality due to the bacterial infection which would be lethal in the absence of treatment.

The pharmaceutical compositions of the present invention show antibacterial activity in one of the above-described assays, particularly in Assay IV.

The pharmaceutical compositions of the invention can be used to treat humans, cattle, horses, sheep, swine, goats, rabbits, cats, dogs, and other mammals in need of such treatment. In particular, the pharmaceutical compositions of the invention can be used to treat, inter alia, bovine respiratory disease, swine respiratory disease, pneumonia, pasteurellosis, coccidiosis, anaplasmosis, and infectious keratinitis. The pharmaceutical compositions may be administered through oral, intramuscular, intravenous, subcutaneous, intra-ocular, parenteral, topical, intravaginal, or rectal routes. For administration to cattle, swine or other domestic animals, the pharmaceutical compositions may be administered in feed or orally as a drench composition. Preferably, the pharmaceutical compositions are injected intramuscularly, intravenously or subcutaneously. In a preferred embodiment, the pharmaceutical compositions are administered in dosages ranging from about 0.5 mg of the equilibrium mixture of isomers per kg of body weight per day (mg/kg/day) to about 20 mg/kg/day. In a more preferred embodiment, the pharmaceutical compositions are administered in dosages ranging from about 1 mg/kg/day to about 10 mg/kg/day. In a most preferred embodiment, the pharmaceutical compositions are administered in dosages ranging from about 1.25 mg/kg/day to about 5.0 mg/kg/day. The pharmaceutical compositions can be administered up to several times per day, for about 1 to about 15 days, preferably about 1 to about 5 days, and repeated where appropriate. Those of skill in the art will readily recognize that variations in dosages can occur depending upon the species, weight and condition of the subject being treated, its individual response to the pharmaceutical compositions, and the particular route of administration chosen. In some instances, dosage levels below the lower limit of the aforesaid ranges may be therapeutically effective, while in other cases still larger doses may be employed without causing any harmful side effects, provided that such larger doses are first divided into several small doses for administration throughout the day.

The following Examples further illustrate the compositions and methods of the present invention. It is to be understood that the present invention is not limited to the specific details of the Examples provided below.

EXAMPLE 1

Synthesis of isomer II. To a 2 L erlenmeyer flask was added desmethylazithromycin (190.5 g, 259.2 mmol), methylene chloride (572 mL), and magnesium sulfate (38 g) The mixture was stirred for 10 min then filtered into a 5 L round bottom flask. Additional methylene chloride (2285 mL) was added and the solution cooled to 0–5° C. CBZ-CI (58.4 mL) (CBZ-CI=benzylchloroformate) was then added over 10 min. The reaction stirred at ≈0° C. for 6 hrs then at ambient temperature overnight. HPLC analysis indicated the presence of residual starting material such that the reaction was re-cooled to ≈0° C. and additional CBZ-CI (19.5 mL) was added in a single portion. The reaction stirred for 5.5 hrs at 0° C. then for 2.5 hrs at ambient temperature. TLC indicated a complete reaction. The reaction was quenched with saturated aqueous sodium bicarbonate (953 mL) and the phases separated. The organic phase was dried over magnesium sulfate, then filtered and concentrated to afford the compound of formula (III):

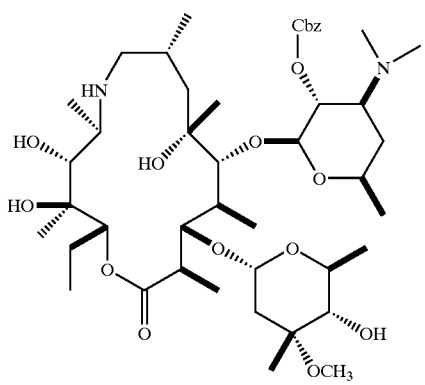

(III)

To a 5 L round bottom flask containing the compound of formula (III) (225.3 g) in methylene chloride (901 mL) and DMSO (450 mL) at −65° C. was added trifluoroacetic anhydride (82.4 mL). The temperature was maintained at −60° C. throughout the addition which was complete in 9 min. The reaction was stirred at −65 to −70° C. for 20 min. The reaction was quenched with triethylamine (145 mL) then stirred at −60° to −65° C. for 20 min. To the reaction mixture was then added water (1127 mL) over 3 min, at which point the temperature rose to −2° C. The reaction mixture was stirred for 10 min and the phases were allowed to separate. The organic phase was washed with water, (675 mL) then with saturated aqueous sodium chloride (675 mL). The organic phase was dried over magnesium sulfate then filtered and organic solvents removed by distillation. MTBE was added and distilled to remove all traces of methylene chloride and DMSO. Additional MTBE was added to a total volume of 3380 mL. Dibenzoyl-D-tartaric acid monohydrate (87.8 g) in MTBE (1126 mL) was added to form a thick slurry. The mixture was heated to reflux and stirred overnight. After cooling to ambient temperature, the solids were collected on a Buchner funnel and rinsed with MTBE. The solids were dried in a drying oven at 40° C. to afford 258.3 g of the dibenzoyl tartrate salt of the compound of formula (IV):

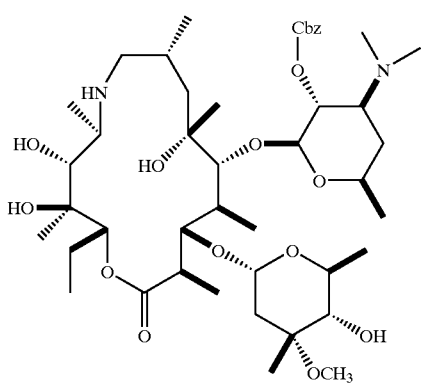

(IV)

To a 3 L round bottom flask was added methylene chloride (800 mL) and the dibenzoyl tartrate salt of the compound of formula (IV) (188 g). Water (400 mL) and potassium carbonate (45.5 g) were added and the mixture stirred at ambient temperature for 5 min. The organic phase was separated, then washed with water (250 mL) and dried over magnesium sulfate. Drying agent was removed by filtration, and the resultant solution evaporated under a stream of nitrogen to a final volume of 623 mL to afford a free-base ketone.

To a 5 L round bottom flask was added THF (623 mL) and trimethylsulfonium bromide (74.7 g). The resultant slurry was cooled to −10° C. and potassium tert-butoxide (54.4 g) added. The reaction mixture was stirred for 10 min at −10° C. then cooled to −70° C. over 5 min. A solution of the free-base ketone was added over 11 min, keeping the temperature between −60 and −65° C. HPLC indicated the reaction was complete after 90 min. The reaction was quenched at −60° C. using a solution of ammonium chloride (315 g) in water (1800 mL). The temperature rose to −5° C. during the quench. The reaction mixture was warmed to 5–10° C., and the phases separated. The organic phase was dried over sodium sulfate then filtered and concentrated to afford the compound of formula (V), (117.4 g) as a yellow foam. HPLC indicated a purity of 61.4% by peak area.

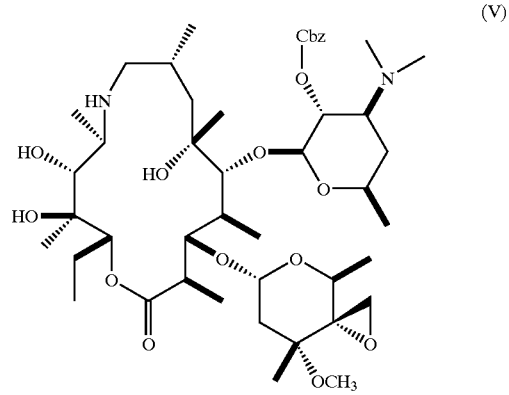

(V)

To a solution of the compound of formula (V) (275 g, 312 mmol) in dry methanol (2.75 L) was added potassium iodide (518 g, 3.12 mol) and n-propylamine (250 mL, 3.04 mol). The mixture was stirred overnight at 45° C. TLC indicated a complete reaction. The reaction was concentrated on a rotary evaporator and the residue partitioned between water (2.5 L) and methylene chloride (2.5 L). The pH of the aqueous phase was adjusted to 6.7 using 3N aqueous HCl. The extraction was repeated one additional time. Combined aqueous phases were combined with fresh methylene chloride (1.5 L) and the pH of the aqueous phase adjusted to 8.5 using solid potassium carbonate. The phases were separated and the aqueous phase re-extracted twice with additional methylene chloride. Combined organic phases were dried over sodium sulfate, then filtered. The filtrate was concentrated on a rotary evaporator to afford a beige foam (230 g). Purification of the foam was effected on a slurry-packed silica gel column using 19/3 (v/v) hexanes-diethylamine as the mobile phase. In this manner, 125 g of crude product afforded 72 g of isomer I as a white, amorphous foam.

Isomer I was dissolved in acetonitrile (0.5 L) at ambient temperature. Deionized water (1 L) was then added, which caused precipitation. Additional acetonitrile (0.5 L) was then added to afford a homogenous solution which was stirred at ambient temperature for 30 hrs. HPLC analysis indicated the formation of a new component that comprised ≈20% total peak area.

Organic solvent was removed on a rotary evaporator. Potassium carbonate (30 g) was added to the aqueous residue followed by methylene chloride (0.3 L). The mixture was shaken and the lower organic phase removed. Two additional extractions (2×0.3 L) were also performed. Combined organic phases were dried over sodium sulfate, then filtered and the resultant solution concentrated to a dry foam (≈10 g).

The resultant mixture of isomer I and isomer II, was dissolved in a mixture of methylene chloride and 19/3 (v/v)

hexanes-diethylamine, and placed on a slurry-packed silica gel column, then eluted with the 19/3 system. The eluant was switched to 19/6 hexanes-diethylamine in fraction 56. Fraction 9–17 were combined and concentrated to a dry foam which contained only unreacted starting material. Fractions 52–72 were combined and concentrated, and contained isomer II (79% purity by HPLC).

EXAMPLE 2

Table 1 below shows the effect of pH, temperature, acid type, and concentration of isomer I on the equilibration reaction rate and on levels of major impurities following equilibration. Replicated experiments (data not shown) demonstrated reproducibility of results. The equilibrium ratio of isomers I and II (about 90%±4% to about 10%±4%, respectively) was consistent for all experiments. Analysis of the data indicates that pH and temperature have a significant effect on the time required for equilibration. Without being bound by any theory, lower equilibration temperatures or lower pH values generally result in substantially longer equilibration times. Equilibration time can also depend on, inter alia, the concentration of starting material, and the type and concentration of the acid used. Isomer I at a concentration of up to about 300 mg per mL of composition was heated to a temperature of about 40° C. to about 80° C. in the presence of one or more acids at a concentration of about 0.2 mmol to about 1.0 mmol per mL of mixture and with a sufficient quantity of hydrochloric acid to achieve a pH of about 6.5 to about 7.5 for up to about 20 hours to produce an equilibrium mixture of isomers that is about 95%–98% pure. Equilibration kinetic parameters and impurity levels for equilibration of azalide isomers I and II were determined as a function of pH, equilibration temperature, type of acid, and isomer I concentration and are listed in Table 1. Known methods, including high performance liquid chromatography ("HPLC"), nuclear magnetic resonance spectroscopy ("NMR"), gas chromatography ("GC"), mass spectrometry ("MS"), liquid chromatography/mass spectrometry ("LC/MS"), GC/MS, and thin layer chromatography ("TLC"), can be used to identify the impurities. "DS" refers to isomer I prior to equilibration and is included for comparison.

Equilibrium mixtures of isomers were prepared and assayed as follows. 40 mL of solution were prepared in each of experiments 1A–11A, and each solution was divided into 1 mL aliquots prior to heating in order to more easily monitor equilibration at different time points. 20 mL of solution were prepared in each of experiments 128–24B, and each solution was divided into 0.7 mL aliquots prior to heating. 100 mL of solution were prepared in each of experiments 25C–28C, 200 mL of solution were prepared in each of experiments 29C–30C, and equilibration was monitored from 0.5 mL aliquots removed from the solutions. 60 mL of solution were prepared in each of experiments 31D–33D and 35D–41D, 170 mL of solution were prepared in experiment 34D, and equilibration was monitored from 0.5 mL aliquots removed from the solutions. From 7,200 mL to 54,000 mL of solution were prepared in each of experiments 42E–46E, and equilibration was monitored by removing from 2 mL to 5 mL aliquots from the solutions. From 35 mL to 50 mL of solution were prepared in each of experiments 47F–50G, and each solution was divided into 1 mL aliquots prior to heating. Water was added to the appropriate container, followed by the type and amount of acid listed in column 4 of Table 1. The term "qs" preceding the acid type refers an amount of the acid sufficient to achieve the pH listed in column 2. Where 0.1 M citric or tartaric acid was used, hydrochloric acid was also added in a quantity sufficient to obtain the pH listed in column 2 Where an acid concentration is recited in column 4 (e.g., "0.1 M citric"), this is the concentration of acid in a solution having an equilibrated mixture of isomer I and isomer II present in a concentration of 100 mg/mL. The mixture of water and acid was stirred until all of the acid was dissolved (about 5 minutes or less for smaller volumes, and about 20 minutes for larger volumes). Isomer I was added slowly and in small portions to avoid clumping, and the resulting mixture was stirred vigorously until dissolved (less than 30 minutes for smaller volumes, and about 60–120 minutes for larger volumes). After dissolution of isomer I, the pH of the resulting solution was measured. If the pH was lower than the pH listed in column 2, it was raised to the pH listed in column 2 with 10% sodium hydroxide. If the pH was higher than the pH listed in column 2, it was lowered with the appropriate acid(s). For each experiment, the solution was heated at the temperature noted in column 3 until an equilibrium mixture of isomers was obtained, as determined by one of the HPLC assays described below. In some experiments, mixtures were heated for a period of time longer than required for equilibration (percentages greater than 100% in column 8) to determine the effects of prolonged heat on the degree of impurity.

To monitor the equilibration of the azalide isomers, reaction mixture aliquots were assayed by HPLC at various times during equilibration. For the majority of equilibration experiments shown in Table 1, aliquots were diluted with 40 mM potassium phosphate buffer (pH 6.0) to a concentration of approximately 0.5 mg of azalide isomers per mL total sample volume and subjected to chromatography using an Asahipak ODP-50, 5 $\mu$m, 250×4.0 mm column (40% acetonitrile/35% methanol/25% 40 mM potassium phosphate; pH 8.5 mobile phase; flow rate 0.7 mL/min; room temperature) on an HP 1090 Liquid Chromatograph equipped with an external Applied Biosystems 783A Programmable Absorbance Detector. Peaks were detected by monitoring ultraviolet absorption at 210 nm. For the remaining equilibration experiments shown in Table 1 (experiments 31D–46E), aliquots were diluted with 20% acetonitrile/50% methanol/30% 50 mM potassium phosphate (pH 5.5) to a concentration of 1.0 mg of azalide isomers per mL of total sample volume and subjected to chromatography using a YMC Pro-Pack $C_{18}$, 3 $\mu$m, 50×2.0 mm column (20% acetonitrile/50% methanol/30% 50 mM potassium phosphate; pH 7.0 mobile phase; flow rate 0.5 mL/min; room temperature) on an HP 1090 Liquid Chromatograph with internal UV Detector. Peaks were detected by monitoring ultraviolet absorption at 210 nm. Relative amounts of isomer I and isomer II were determined by taking the ratio of their relative chromatogram-peak areas. Under the above HPLC conditions, isomer I has a retention time of approximately 13–23 minutes, and isomer II has a relative retention time ("RRT") of approximately 0.8 to 0.9. By "RRT" is meant a retention time relative to that of isomer I under the above-described HPLC conditions.

The purity of equilibrated samples in Table 1 was determined using HPLC according to one of three procedures. In experiments 1A–24B, 48F, and 50G, aliquots were diluted with 25 mM potassium phosphate buffer (pH 5.5) to a concentration of 1.25 mg of azalide isomers per mL total sample volume and assayed using an Eclipse XDB-$C_8$, 5 $\mu$m, 250×4.6 mm column (22% acetonitrile/58% methanol/20% 25 mM potassium phosphate; pH 8.0 mobile phase; flow rate 0.6 mL/min; room temperature) on a Waters Alliance 2690 Separation Module with BAS CC-5/LC-4C Amperometric Detector. Peaks were detected electrochemically with one electrode at +0.70 V, a second electrode at +0.88 V, and a range of 0.5 µA. In experiments 25C–41D, aliquots were diluted with 50 mM citric acid (pH 5.5) to a concentration of 0.25 mg azalide isomers per mL of total sample volume and assayed using a YMC Pro-Pack $C_{18}$, 3 µm, 150×4.6 mm column (70% methanol/30% 50 mM phosphate, pH 70 mobile phase; flow rate 1 mL/min; room temperature) on the Waters Alliance system. Peaks were detected electrochemically with only one electrode at +0.90 V. In experiments 42E–43E, aliquots were diluted with 50 mM citric acid (pH 5.5) to a concentration of 0.25 mg azalide isomers per mL of total sample volume and assayed using a YMC Pro-Pack $C_{18}$, 3 µm, 150×4.6 mm column (70% methanol/30% 50 mM phosphate; pH 7.0 mobile phase; flow rate 1 mL/min; room temperature) on an HP 1090 Liquid Chromatograph with BAS CC-5/LC-4C Amperometric Detector. Peaks were detected electrochemically with only one electrode at +0.90 V. The percentage of the equilibrium mixture of isomers (column 9) and impurities (column 10) relative to the assayed sample was determined using the areas under the peaks in the chromatograms. Some of the detected impurities were: a descladinose azalide (its RRT being approximately 0.26 on an Eclipse $XDB-C_8$ column), an acetaldehyde insertion product (its RRT being approximately 1.75 on an Eclipse $XDB-C_8$ column), and a formaldehyde insertion product (its RRT being approximately 1.6 on an Eclipse $XDB-C_8$ column).

The descladinose azalide has the structure:

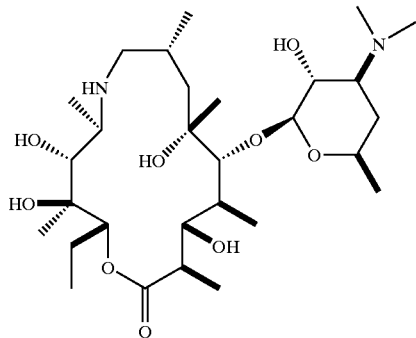

The acetaldehyde insertion product has the structure:

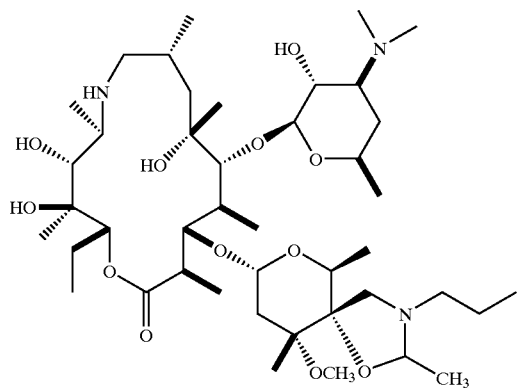

The formaldehyde insertion product has the structure:

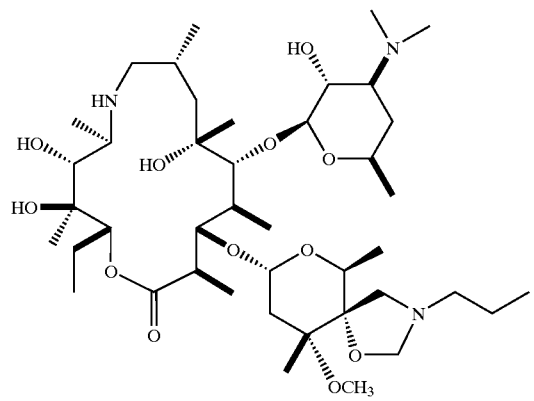

The descladinose azalide, the acetaldehyde insertion product, and the formaldehyde insertion product, and pharmaceutically acceptable salts thereof, have antibiotic properties and are useful as antibiotic agents.

The experiments of groups A and B (identified by the letter following the experiment number) in Table 1 were performed to determine the effects of pH, temperature, type of acid, concentration of acid, and isomer I concentration on equilibration. The experiments of group C in Table 1 illustrate the effects of pH and temperature on equilibration. The experiments of group D in Table 1 illustrate the effects of pH, temperature, and acid concentration on equilibration. The experiments of group E in Table 1 illustrate a preferred method of equilibration, that is, at a pH of about 7.0, an equilibration temperature of about 70° C., and an isomer I concentration of about 250 mg/mL. Experiments in group F tested the effects of alternate acids and equilibration temperatures, and experiment G was performed in the presence of 50% propylene glycol co-solvent.

Results of these experiments indicate that, even under a variety of conditions, equilibration of the azalide isomers consistently results in the formation of from about 90%±4% of isomer I and about 10%±4% of isomer II. Equilibration temperature and pH appear to have the largest effect on equilibration rate, with higher temperatures generally leading to faster rates, even with higher concentrations of isomer I. In most cases, however, longer equilibration times resulted in higher concentration of impurities, and therefore, optimal equilibration conditions are those leading to relatively high equilibration rates, i.e., that form the equilibrium mixture of isomers in 1–3 hours.

TABLE 1

| Experiment Number & Group | pH | Equil. temp (° C.) | acid | Initial isomer I concentration (mg/mL) | % of isomer II at equil. | Time to equilibration (hrs) | % of time to equilibration | % Equilibrium mixture of isomers | % Impurities |
|---|---|---|---|---|---|---|---|---|---|
| DS |  |  |  |  |  |  |  | 98.39 | 1.61 |
| 1A | 6.3 | 65 | qs citric | 112 | 12.2 | 5.1 | 100 | 96.09 | 3.91 |
|  |  |  |  |  |  |  | 150 | 94.03 | 5.34 |
| 2A | 6.0 | 80 | qs phosphoric | 75 | 11.6 | 2 | 100 | 94.57 | 5.43 |
|  |  |  |  |  |  |  | 370 | 86.71 | 13.29 |
| 3A | 7.0 | 70 | qs citric | 75 | 11.5 | 1.4 | 100 | 96.36 | 3.64 |
|  |  |  |  |  |  |  | 640 | 89.62 | 10.38 |
| 4A | 7.0 | 50 | qs citric | 150 | 11.5 | 10.9 | 100 | 97.76 | 2.24 |
|  |  |  |  |  |  |  | 200 | 96.94 | 3.06 |
| 5A | 6.0 | 60 | qs phosphoric | 150 | 11.2 | 12.9 | 100 | 96.52 | 3.48 |
|  |  |  |  |  |  |  | 170 | 95.18 | 4.82 |
| 6A | 6.0 | 60 | qs citric | 75 | 12.3 | 17.6 | 100 | 96.15 | 3.85 |
|  |  |  |  |  |  |  | 170 | 94.95 | 5.05 |
| 7A | 6.0 | 80 | qs citric | 150 | 11.9 | 2.2 | 100 | 96.15 | 3.85 |
|  |  |  |  |  |  |  | 160 | 95.20 | 4.80 |
| 8A | 7.0 | 50 | Qs phosphoric | 75 | 11.4 | 7.2 | 100 | 97.79 | 2.21 |
|  |  |  |  |  |  |  | 150 | 96.47 | 3.53 |
| 9A | 7.0 | 70 | qs phosphoric | 150 | 12.1 | 1.2 | 100 | 97.66 | 2.34 |
|  |  |  |  |  |  |  | 160 | 96.70 | 3.30 |
| 10A | 6.5 | 65 | qs citric | 112 | 11.3 | 3.3 | 100 | 96.63 | 3.37 |
|  |  |  |  |  |  |  | 190 | 96.64 | 3.36 |
| 11A | 6.5 | 65 | qs citric | 112 | 12.4 | 3.6 | 100 | 96.87 | 3.13 |
|  |  |  |  |  |  |  | 200 | 94.76 | 5.24 |
| 12B | 7.0 | 70 | qs citric | 150 | 12.5 | 1.4 | 100 | 94.33 | 5.67 |
|  |  |  |  |  |  |  | 150 | 94.00 | 6.00 |
| 13B | 7.25 | 65 | 0.1 M citric/ qs HCl | 225 | 11.2 | 3.3 | 100 | 94.55 | 5.45 |
|  |  |  |  |  |  |  | 150 | 94.26 | 5.74 |
| 14B | 7.25 | 65 | qs citric | 225 | 11.2 | 2.5 | 100 | 94.75 | 5.25 |
|  |  |  |  |  |  |  | 150 | 94.17 | 5.83 |
| 15B | 7.0 | 70 | 0.1 M citric/ qs HCl | 300 | 11.0 | 3.6 | 100 | 93.08 | 6.92 |
|  |  |  |  |  |  |  | 150 | 92.74 | 7.26 |
| 16B | 7.5 | 70 | 0.1 M citric/ qs HCl | 150 | 11.6 | 1.4 | 100 | 94.98 | 5.02 |
|  |  |  |  |  |  |  | 150 | 94.82 | 5.18 |
| 17B | 7.0 | 60 | qs HCl | 300 | 11.4 | 4.9 | 100 | 93.93 | 6.07 |
|  |  |  |  |  |  |  | 150 | 93.80 | 6.20 |
| 18B | 7.5 | 60 | qs citric | 150 | 12.1 | 2.6 | 100 | 94.00 | 6.00 |
|  |  |  |  |  |  |  | 150 | 93.89 | 6.11 |
| 19B | 7.5 | 60 | 0.1 M citric/ qs HCl | 300 | 11.3 | 4.5 | 100 | 93.89 | 6.11 |
|  |  |  |  |  |  |  | 150 | 93.78 | 6.22 |
| 20B | 7.5 | 70 | qs citric | 300 | 11.3 | 1.5 | 100 | 93.88 | 6.12 |
|  |  |  |  |  |  |  | 150 | 93.65 | 6.35 |
| 21B | 7.0 | 60 | 0.1 M citric/ qs HCl | 150 | 12.3 | 4.1 | 100 | 94.31 | 5.69 |
|  |  |  |  |  |  |  | 150 | 94.27 | 5.73 |
| 22B | 7.25 | 65 | 0.1 M citric/ qs HCl | 225 | 11.7 | 3.0 | 100 | 94.51 | 5.49 |
|  |  |  |  |  |  |  | 150 | 94.24 | 5.76 |
| 23B | 7.25 | 65 | Citric | 225 | 12.3 | 2.3 | 100 | 94.23 | 5.77 |
|  |  |  |  |  |  |  | 150 | 94.10 | 5.90 |

TABLE 1-continued

| Experiment Number & Group | pH | Equil. temp (° C.) | acid | Initial isomer I concentration (mg/mL) | % of isomer II at equil. | Time to equilibration (hrs) | % of time to equilibration | % Equilibrium mixture of isomers | % Impurities |
|---|---|---|---|---|---|---|---|---|---|
| 24B | 7.0 | 70 | Citric | 300 | 11.4 | 2.2 | 100 | 94.43 | 5.57 |
| 25C | 7.5 | 75 | 0.1 M citric/ qs HCl | 250 | 11.8 | 1.3 | 150 | 93.91 | 6.09 |
| 26C | 7.5 | 65 | 0.1 M citric/ qs HCl | 250 | 10.5 | 3.0 | 100 | 98.59 | 1.41 |
| 27C | 6.5 | 75 | 0.1 M citric/ qs HCl | 250 | n/a | 4.0 | 85 | 98.78 | 1.22 |
| 28C | 6.5 | 65 | 0.1 M citric/ qs HCl | 250 | n/a | 9.9 | 50 | 98.74 | 1.26 |
| 29C | 7.0 | 70 | 0.1 M citric/ qs HCl | 250 | 11.1 | 1.8 | 100 | 98.91 | 1.09 |
| 30C | 7.0 | 70 | 0.1 M citric/ qs HCl | 250 | 11.3 | 2.2 | 100 | 98.90 | 1.10 |
| 31D | 7.0 | 70 | 0.125 M citric/ qs HCl | 250 | 10.2 | 2.6 | 100 | 98.91 | 1.09 |
| 32D | 7.0 | 70 | 0.125 M citric/ qs HCl | 250 | 10.1 | 2.8 | 100 | — | — |
| 33D | 7.0 | 70 | 0.125 M citric/ qs HCl | 250 | 10.2 | 2.6 | 100 | — | — |
| 34D | 7.0 | 70 | 0.175 M citric/ qs HCl | 250 | 10.5 | 2.5 | 100 | — | — |
| 35D | 7.0 | 70 | 0.1 M citric/ qs HCl | 250 | 10.6 | 2.2 | 100 | — | — |
| 36D | 7.5 | 75 | 0.1 M citric/ qs HCl | 250 | 11.2 | 1.0 | 100 | — | — |
| 37D | 7.5 | 65 | 0.1 M citric/ qs HCl | 250 | 11.1 | 1.9 | 100 | — | — |
| 38D | 7.0 | 70 | 0.1 M citric/ qs HCl | 250 | 10.8 | 2.4 | 100 | — | — |
| 39D | 8.0 | 70 | 0.1 M citric/ qs HCl | 250 | 11.1 | 1.1 | 100 | — | — |
| 40D | 6.5 | 70 | 0.1 M citric/ qs HCl | 250 | 10.6 | 1.9 | 100 | — | — |
| 41D | 6.5 | 65 | 0.1 M citric/ qs HCl | 250 | 10.8 | 5.8 | 100 | — | — |
| 42E | 7.0 | 70 | 0.1 M citric/ qs HCl | 250 | 11.6 | 1.1 | 100 | 96.00 | 4.00 |
| 43E | 7.5 | 70 | 0.1 M tartaric/ qs HCl | 250 | 12.0 | 2.0 | 100 | 94.90 | 5.10 |
| 44E | 7.0 | 70 | 0.1 M citric/ qs HCl | 250 | 13.6 | 1.4 | 100 | — | — |

TABLE 1-continued

| Experiment Number & Group | pH | Equil. temp (° C.) | acid | Initial isomer I concentration (mg/mL) | % of isomer II at equil. | Time to equilibration (hrs) | % of time to equilibration | % Equilibrium mixture of isomers | % Impurities |
|---|---|---|---|---|---|---|---|---|---|
| 45E | 6.8 | 70 | 0.1 M citric/ qs HCl | 250 | 12.7 | 1.1 | 100 | — | — |
| 46E | 6.9 | 70 | 0.1 M citric/ qs HCl | 250 | 12.4 | 1.3 | 100 | — | — |
| 47F | 7 | 70 | qs citric | 250 | 10.8 | 1.4 | 100 | 94.78 | 5.22 |
| 48F | 7 | 70 | 0.1 M tartaric/ qs HCl | 250 | 11.5 | 7.7 | 100 | — | — |
| 49F | 7.4 | 39 | qs phosphoric | 1 | 11.1 | 6.7 | 100 | — | — |
| 50G | 7 | 70 | qs citric | 75 | 9.4 | 2.7 | 100 | — | — |

EXAMPLE 3

The stability of equilibrated compositions stored at 50° C. for 12 weeks and stabilized with co-solvent is shown in Table 2 below. The results indicate that the compositions containing no co-solvent are significantly less stable than compositions containing co-solvent in an amount of from about 250 to about 500 mg per mL of the composition (experiments 1A–11B). Compositions having a pH of about 5.4 and containing propylene glycol ("PG") in an amount of from about 450 to about 550 mg per mL of the composition are the most stable. Other co-solvents may be used to stabilize the compositions (experiments 1E–2E); however, propylene glycol is preferred. As shown in Table 2, stability is dependent on pH, and it can also be dependent on type and quantity of acid used, and concentration of the equilibrated mixture of isomers.

These compositions were prepared as follows. After heating to the desired temperature (column 2) and allowing the mixture of water, acid, and isomer I to equilibrate for the time shown in column 3, equilibrium mixtures of isomers were allowed to cool to room temperature. When the mixtures reached room temperature, the appropriate amount of the desired co-solvent was added (column 6). The percentage of co-solvent shown in column 6 is a weight-to-volume percentage (e.g., 50% PG is 500 mg propylene glycol per mL of pharmaceutical composition). If an antioxidant or a preservative was used, the appropriate amounts were added (columns 8 and 9). The pH of the solution was measured and adjusted to the value in column 5 by adding one or more acids and/or 10% w/w sodium hydroxide. The volumes of the resulting solutions were then adjusted by adding water. The compositions were filtered through a 0.2 micron sterilizing filter. Vials were filled in a laminar-flow hood, and the vial head space was flushed with the appropriate gas mixture (column 10) before sealing.

Equilibration and purity were monitored using HPLC as described above in Example 2. The stability of stabilized, equilibrated compositions sealed in glass vials was determined after storage for 12 weeks at 50° C. The effects of concentration of the equilibrium mixture of isomers, pH, co-solvent amount and type, type and concentration of acid, exposure to air, presence of preservatives, and presence of antioxidants were monitored. Results are shown in Table 2.

Experiments 1A–3A were performed to monitor the effect of equilibrium mixture concentration on stability. experiments 2A, 6A, and 7A were performed to monitor the effect of pH on stability. Experiments 2A, 4A, and 5A show the effect of co-solvent amount on stability, and experiments 3A and 8A show the effect of using citric acid alone, as opposed to mixtures of citric and phosphoric acid, for obtaining an acidic pH. Experiments 1B–11B show the effects of pH and propylene glycol ("PG") co-solvent on stability. Experiments 1C and 2C show the effect of using tartaric acid alone, as opposed to a mixture of tartaric and hydrochloric acid, for obtaining an acidic pH. Experiments 9B–11B and 3C show the effects of a preservative on stability of the mixture, and experiments 9B–11B, 4C, and 5C show the effects of an antioxidant on stability of the mixture. Experiments 6C and 7C show the effects of using a mixture of tartaric and hydrochloric acid or a mixture of citric and hydrochloric acid on stability. Experiments 1D–12D show the effects of different amounts of monothioglycerol ("MTG") antioxidant and different degrees of oxygen exposure on stability. Experiments 4D–6D and 13D–18D demonstrate the effects of pH of the composition and acid concentration on stability.

Results of these experiments indicate that after storage for 12 weeks at 50° C., the equilibrated compositions that contain at least 50% propylene glycol and have a pH ranging from about 5.2 to about 5.5 retain greater than 93% of the initial concentration of the equilibrium mixture of isomers. The highest level of impurities was found in a composition having no co-solvent (experiment 4A). Accordingly, the presence of co-solvent surprisingly and unexpectedly limits the amount of impurities. High levels of impurities were found after 12 weeks in compositions having less than 40% co-solvent and a pH of less than 5.0. The concentration of the acid also affects stability of the pharmaceutical compositions. Compositions with relatively low concentrations of acid (about 20 mM) and a pH of about 5.4 show the greatest stability after storage. However, low acid concentrations result in low buffer strength, which leads to fluctuating pH and may lead to a relatively high degree of impurity under other time or temperature conditions.

TABLE 2

| Experiment number and Group | Equil. Temp (° C.) | Equil. Time (hrs) | Concentration of equilibrium mixture of isomers in pharmaceutical comp. | pH | Co-solvent type and amount | Acid Concentration (M) | Preservative | Antioxidant (mg/mL) | Headspace Filler | % at 12 weeks and 50° C. isomer II | isomer I | Equilibrium Mixture of Isomers | % Impurities |
|---|---|---|---|---|---|---|---|---|---|---|---|---|---|
| 1A | 60 | 16 | 10 | 5.0 | 50% PG | qs citric | — | — | $N_2$ | 12.33 | 80.48 | 92.81 | 7.19 |
| 2A | 60 | 16 | 30 | 5.0 | 50% PG | qs citric | — | — | $N_2$ | 12.09 | 77.88 | 89.97 | 10.03 |
| 3A | 60 | 16 | 100 | 5.0 | 50% PG | qs citric | — | — | $N_2$ | 11.95 | 76.13 | 88.08 | 11.92 |
| 4A | 60 | 16 | 30 | 5.0 | — | qs citric | — | — | $N_2$ | 12.78 | 66.44 | 79.22 | 20.78 |
| 5A | 60 | 16 | 30 | 5.0 | 25% PG | qs citric | — | — | $N_2$ | 13.07 | 75.50 | 88.57 | 11.43 |
| 6A | 60 | 16 | 30 | 4.5 | 50% PG | qs citric | — | — | $N_2$ | 10.71 | 76.71 | 87.42 | 12.58 |
| 7A | 60 | 16 | 30 | 5.5 | 50% PG | 0.23 M citric/ 0.23 M citric | — | — | $N_2$ | 11.81 | 80.34 | 92.15 | 7.85 |
| 8A | 60 | 24 | 100 | 5.0 | 50% PG | qs $H_3PO_4$ | — | — | $N_2$ | 11.80 | 74.27 | 86.07 | 13.93 |
| 1B | 70 | 1.5 | 100 | 5.0 | 25% PG | qs citric | — | — | $N_2$ | 10.90 | 79.50 | 90.40 | 9.60 |
| 2B | 70 | 1.5 | 100 | 5.0 | 50% PG | qs citric | — | — | $N_2$ | 9.10 | 83.20 | 92.30 | 7.70 |
| 3B | 70 | 1.5 | 100 | 5.5 | 25% PG | qs citric | — | — | $N_2$ | 10.70 | 81.40 | 92.10 | 7.90 |
| 4B | 70 | 1.5 | 100 | 5.5 | 50% PG | qs citric | — | — | $N_2$ | 9.50 | 83.80 | 93.30 | 6.70 |
| 5B | 70 | 1.5 | 100 | 5.25 | 20% PG | qs citric | — | — | $N_2$ | 10.90 | 79.70 | 90.60 | 9.40 |
| 6B | 70 | 1.5 | 100 | 5.25 | 55% PG | qs citric | — | — | $N_2$ | 9.30 | 84.40 | 93.70 | 6.30 |
| 7B | 70 | 1.5 | 100 | 4.75 | 37.5% PG | qs citric | — | — | $N_2$ | 9.70 | 79.40 | 89.10 | 10.90 |
| 8B | 70 | 1.5 | 100 | 5.75 | 37.5% PG | qs citric | — | — | $N_2$ | 9.90 | 82.70 | 92.60 | 7.40 |
| 9B | 70 | 1.5 | 100 | 5.25 | 37.5% PG | qs citric | — | — | $N_2$ | 9.50 | 83.10 | 92.60 | 7.40 |
| 10B | 70 | 1.5 | 100 | 5.25 | 37.5% PG | qs citric | — | — | $N_2$ | 9.90 | 81.70 | 91.60 | 8.40 |
| 11B | 70 | 1.5 | 100 | 5.25 | 37.5% PG | qs citric | — | — | $N_2$ | 10.20 | 82.20 | 92.40 | 7.60 |
| 1C | 70 | 1.5 | 100 | 5.25 | 37.5% PG | qs tartaric | — | — | $N_2$ | 10.10 | 83.40 | 93.50 | 6.50 |
| 2C | 70 | 1.5 | 100 | 5.25 | 37.5% PG | 0.1 M tartaric/ qs HCl | — | — | $N_2$ | 10.00 | 84.30 | 94.30 | 5.70 |
| 3C | 70 | 1.5 | 100 | 5.25 | 37.5% PG | qs citric | phenol | — | — | 10.40 | 89.60 | 100.00 | — |
| 4C | 70 | 1.5 | 100 | 5.25 | 37.5% PG | qs citric | — | — | $N_2$ | 9.90 | 83.00 | 92.90 | 7.10 |
| 5C | 70 | 1.5 | 100 | 5.25 | 37.5% PG | qs citric | — | 5 MTG | $N_2$ | 9.90 | 83.00 | 92.90 | 7.10 |
| 6C | 70 | 1.5 | 100 | 5.50 | 50% PG | 0.1 M tartaric/ qs HCl | — | 5 propyl gallate 5 MTG | $N_2$ | 8.40 | 88.20 | 96.60 | 3.40 |
| 7C | 70 | 1.5 | 100 | 5.50 | 50% PG | 0.1 M citric/ qs HCl | — | 5 MTG | $N_2$ | 8.40 | 88.80 | 97.20 | 2.80 |
| 1D | 70 | 1.5 | 100 | 5.40 | 50% PG | 0.1 M citric/ qs HCl | — | 10 MTG | air | 9.02 | 87.40 | 96.42 | 3.58 |
| 2D | 70 | 1.5 | 100 | 5.40 | 50% PG | 0.1 M citric/ qs HCl | — | 10 MTG | 5% $O_2$ | 9.03 | 87.40 | 96.43 | 3.57 |
| 3D | 70 | 1.5 | 100 | 5.40 | 50% PG | 0.1 M citric/ qs HCl | — | 5 MTG | air | 9.07 | 87.17 | 96.24 | 3.76 |

TABLE 2-continued

| Experiment number and Group | Equil. Temp (° C.) | Equil. Time (hrs) | Concentration of equilibrium mixture of isomers in pharmaceutical comp. | pH | Co-solvent type and amount | Acid Concentration (M) | Preservative | Antioxidant (mg/mL) | Headspace Filler | % at 12 weeks and 50° C. isomer II | % at 12 weeks and 50° C. isomer I | Equilibrium Mixture of Isomers | % Impurities |
|---|---|---|---|---|---|---|---|---|---|---|---|---|---|
| 4D | 70 | 1.5 | 100 | 5.40 | 50% PG | 0.1 M citric/qs HCl | — | 5 MTG | 10% $O_2$ | 9.13 | 87.25 | 96.38 | 3.62 |
| 5D | 70 | 1.5 | 100 | 5.40 | 50% PG | 0.1 M citric/qs HCl | — | 5 MTG | 10% $O_2$ | 9.14 | 87.38 | 96.52 | 3.48 |
| 6D | 70 | 1.5 | 100 | 5.40 | 50% PG | 0.1 M citric/qs HCl | — | 5 MTG | 10% $O_2$ | 9.14 | 87.44 | 96.58 | 3.42 |
| 7D | 70 | 1.5 | 100 | 5.40 | 50% PG | 0.1 M citric/qs HCl | — | 5 mM MTG | 5% $O_2$ | 9.20 | 87.16 | 96.36 | 3.64 |
| 8D | 70 | 1.5 | 100 | 5.40 | 50% PG | 0.1 M citric/qs HCl | — | 5 MTG | 1% $O_2$ | 9.20 | 87.14 | 96.34 | 3.66 |
| 9D | 70 | 1.5 | 100 | 5.40 | 50% PG | 0.1 M citric/qs HCl | — | 2.5 MTG | air | 9.19 | 87.17 | 96.36 | 3.64 |
| 10D | 70 | 1.5 | 100 | 5.40 | 50% PG | 0.1 M citric/qs HCl | — | 2.5 MTG | 5% $O_2$ | 9.24 | 87.14 | 96.38 | 3.62 |
| 11D | 70 | 1.5 | 100 | 5.40 | 50% PG | 0.1 M citric/qs HCl | — | — | air | 9.18 | 86.94 | 96.12 | 3.88 |
| 12D | 70 | 1.5 | 100 | 5.40 | 50% PG | 0.1 M citric/qs HCl | — | — | 5% $O_2$ | 9.18 | 86.92 | 96.10 | 3.90 |
| 13D | 70 | 1.5 | 100 | 5.70 | 50% PG | 0.1 M citric/qs HCl | — | 5 MTG | 10% $O_2$ | 9.18 | 86.96 | 96.14 | 3.86 |
| 14D | 70 | 1.5 | 100 | 5.10 | 50% PG | 0.1 M citric/qs HCl | — | 5 MTG | 10% $O_2$ | 9.20 | 87.05 | 96.25 | 3.75 |
| 15D | 70 | 1.5 | 100 | 5.40 | 50% PG | 0.05 M citric/qs HCl | — | 5 MTG | 10% $O_2$ | 9.21 | 87.44 | 96.65 | 3.35 |
| 16D | 70 | 1.5 | 100 | 5.70 | 50% PG | 0.025 M citric/qs HCl | — | 5 MTG | 10% $O_2$ | 9.11 | 87.51 | 96.62 | 3.38 |
| 17D | 70 | 1.5 | 100 | 5.10 | 50% PG | 0.025 M citric/qs HCl | — | 5 MTG | 10% $O_2$ | 9.11 | 86.79 | 95.90 | 4.10 |
| 18D | 70 | 1.5 | 100 | 5.40 | 50% PG | 0.025 M citric/qs HCl | — | 5 MTG | 10% $O_2$/air | 9.07 | 87.86 | 96.93 | 3.07 |
| 1E | | | 30 | 5.0 | 50% glycerol formal | qs citric | — | — | | | | 99.7 | |
| 2E | | | 30 | 5.0 | 50% N-methyl pyrrolidone | qs citric | — | — | air | | | 94.9 | |

EXAMPLE 4

Fifty-two liters of an injectable pharmaceutical composition containing 100 mg of equilibrium mixture of isomers per mL of composition were prepared as follows. 16.584 kg of Water for Injection (USP grade) sparged with nitrogen (NF grade) was added to a stainless steel compounding vessel and agitation was begun. Nitrogen was also used as an overlay to reduce oxygen exposure of the solution in the compounding vessel during manufacture. Approximately 1 kg of anhydrous citric acid (USP grade) was added to the water and the resulting mixture was agitated until the acid dissolved. 1.511 kg of a 10% (w/w) solution of hydrochloric acid (NF grade) in water (USP grade) was subsequently added to the mixture. 5.357 kg of a mixture containing approximately 97% of isomer I and isomer II (in a ratio of about 99:1) and 3% of one or more impurities was slowly added to the agitating mixture and was allowed to dissolve. The pH of the resulting solution was adjusted to 7.0±0.5 by adding 0.224 kg of a 10% (w/w) solution of hydrochloric acid in water. Equilibration of isomers I and II was achieved by heating the solution to 70° C.±10° C. for 105 minutes. Once equilibration was complete, as determined using HPLC, the solution was allowed to cool to 25° C.±10° C., and 26.008 kg of propylene glycol (USP grade) was added to the agitating mixture. After the propylene glycol was completely mixed in, 0.26 kg of monothioglycerol (NF grade) was added to the solution, and the pH was readjusted to 5.4±0.3 by adding 2.349 kg of 10% (w/w) hydrochloric acid in water. The final volume was adjusted to 52.015 liters by adding 1.843 kg of water. The resulting composition contained 100 mg of the equilibrium mixture of isomers per mL of composition, 500 mg per mL of propylene glycol, citric acid at a concentration of 0.1 M, and monothioglycerol at a concentration of 5 mg/mL of composition.

The composition was filtered through a 6 micron pre-filter and then through a 0.2 micron final sterilizing filter, which was sterilized by moist-heat autoclaving for 60 minutes at 121° C. and tested for integrity using the pressure-hold method both prior to sterilization and after filtration. 20 mL flint type I serum glass vials (Wheaton Science Products, Millville, N.J.) were sterilized and depyrogenated in a dry heat tunnel at 250° C. for 240 minutes. 20 mm 4432/50 gray chlorobutyl siliconized stoppers (The West Company, Lionville, Pa.) were depyrogenated by washing and were sterilized by moist-heat autoclaving for 60 minutes at 121° C. Each of 2,525 vials was filled under sterile conditions with 20 mL of the resulting composition plus 0.6 mL overfill (20.6 mL/vial is 2.06 g/vial unit potency of pharmaceutical composition at 100 mg/mL of equilibrium mixture of isomers based on an actual drug substance lot potency of 97.1%), the vial head spaces were flushed with nitrogen, and the vials were sealed with the stoppers and overseals (20 mm aluminum seals, product # 5120-1125, The West Company, Lionville, Pa.).

The present invention is not to be limited in scope by the specific embodiments disclosed in the Examples, which are intended as illustrations of a few aspects of the invention. Any embodiments which are functionally equivalent are within the scope of this invention. Indeed, various modifications of the invention in addition to those shown and described herein will become apparent to those skilled in the art and are intended to fall within the appended claims.

All references disclosed herein are hereby incorporated by reference in their entirety.

What is claimed is:

1. A compound of the formula:

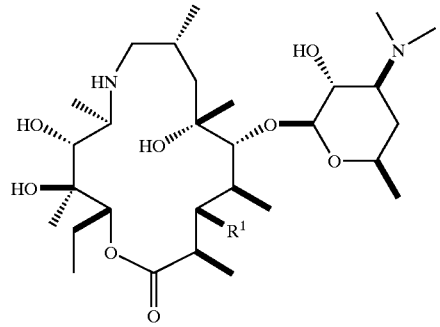

or a pharmaceutically acceptable salt thereof; wherein $R^1$ is

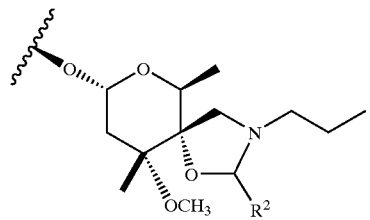

and wherein $R^2$ H or $CH_3$.

* * * * *